(12) United States Patent
Onobori et al.

(10) Patent No.: US 10,136,866 B2
(45) Date of Patent: Nov. 27, 2018

(54) RADIATION IRRADIATION DEVICE

(71) Applicant: FUJIFILM Corporation, Tokyo (JP)

(72) Inventors: Noriyuki Onobori, Kanagawa (JP);
Ryosuke Ogura, Kanagawa (JP);
Takeyasu Kobayashi, Kanagawa (JP);
Yusuke Kitagawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/963,104

(22) Filed: Apr. 26, 2018

(65) Prior Publication Data

US 2018/0235558 A1 Aug. 23, 2018

Related U.S. Application Data

(63) Continuation of application No. PCT/JP2016/083450, filed on Nov. 11, 2016.

(30) Foreign Application Priority Data

Nov. 26, 2015 (JP) .................................. 2015-230363
Apr. 12, 2016 (JP) .................................. 2016-079680

(51) Int. Cl.
*A61B 6/00* (2006.01)

(52) U.S. Cl.
CPC .............. *A61B 6/4405* (2013.01); *A61B 6/40* (2013.01); *A61B 6/4283* (2013.01); *A61B 6/4452* (2013.01)

(58) Field of Classification Search
CPC ........ A61B 6/44; A61B 6/4405; A61B 6/4458
See application file for complete search history.

(56) References Cited

U.S. PATENT DOCUMENTS 3,801,790 A * 4/1974 Gotzl ..................... A61B 6/105
378/117
4,387,468 A * 6/1983 Fenne .................... A61B 6/447
378/198

(Continued)

FOREIGN PATENT DOCUMENTS

JP H10-99312 4/1998
JP H11-76220 3/1999

(Continued)

OTHER PUBLICATIONS

"International Search Report (Form PCT/ISA/210) of PCT/JP2016/083450", dated Feb. 7, 2017, with English translation thereof, pp. 1-4.

(Continued)

*Primary Examiner* — Thomas R Artman
(74) *Attorney, Agent, or Firm* — JCIPRNET (57) ABSTRACT

A radiation irradiation device includes a radiation generation unit; an arm part; a support member having one end to which the arm part is connected; a body part to which the support member is connected; and a leg part on which the body part is placed. The leg part includes first casters that are provided on a front side of the leg part and second casters that are provided on a rear side of the leg part. The diameter of wheels of the second casters and is greater than the diameter of wheels of the first casters, and the gravity center position of the entire device is closer to the second casters side than a center between the first casters and the second casters in a state where the arm part is rotationally moved until the radiation generation unit is located at a vertically lowermost position.

20 Claims, 4 Drawing Sheets

(56) References Cited

U.S. PATENT DOCUMENTS

| | | | | |
|---|---|---|---|---|
| 5,081,662 A * | 1/1992 | Warden | A61B 6/4405 | 378/193 |
| 5,265,149 A * | 11/1993 | Varisco | A61B 6/4405 | 378/193 |
| 5,506,883 A * | 4/1996 | Exner | A61B 6/4405 | 378/197 |
| 5,583,909 A * | 12/1996 | Hanover | A61B 6/4405 | 378/193 |
| 5,627,873 A * | 5/1997 | Hanover | A61B 6/4405 | 378/196 |
| 6,131,690 A | 10/2000 | Galando | A61B 6/4405 | 180/19.1 |
| 6,374,937 B1 * | 4/2002 | Galando | A61B 6/4405 | 180/19.1 |
| 6,715,917 B1 * | 4/2004 | Sohal | A61B 6/4441 | 378/197 |
| 7,607,832 B2 * | 10/2009 | Jensen | A61B 6/4405 | 378/197 |
| 7,611,282 B2 * | 11/2009 | Koren | A61B 6/4233 | 378/198 |
| 8,840,304 B2 * | 9/2014 | Perez Zarate | A61B 6/4405 | 378/197 |
| 8,876,379 B2 * | 11/2014 | DiRisio | A61B 6/447 | 378/193 |
| 9,480,445 B2 * | 11/2016 | Guldstrand | A61B 6/4405 | |
| 2008/0123819 A1 * | 5/2008 | Jensen | A61B 6/4405 | 378/198 |
| 2009/0034688 A1 * | 2/2009 | Koren | A61B 6/4233 | 378/198 |
| 2011/0249807 A1 * | 10/2011 | Dirisio | A61B 6/4405 | 378/198 |
| 2011/0306864 A1 * | 12/2011 | Zarate | A61B 6/4405 | 600/407 |
| 2013/0003939 A1 * | 1/2013 | Bouvier | A61B 6/4405 | 378/198 |
| 2013/0094630 A1 * | 4/2013 | Limmer | H05G 1/02 | 378/198 |
| 2013/0136240 A1 * | 5/2013 | Causape Rodriguez | A61B 6/4405 | 378/198 |
| 2014/0291539 A1 | 10/2014 | Omura | | |
| 2014/0348304 A1 * | 11/2014 | Guldstrand | A61B 6/4405 | 378/198 |
| 2016/0113605 A1 * | 4/2016 | Bouvier | A61B 6/4405 | 378/198 |
| 2017/0086764 A1 * | 3/2017 | Bouvier | A61B 6/4405 | |
| 2017/0360386 A1 * | 12/2017 | Ninomiya | A61B 6/547 | |
| 2017/0374728 A1 * | 12/2017 | Kuranisi | A61B 6/4405 | |
| 2018/0000434 A1 * | 1/2018 | Ninomiya | A61B 6/4405 | |
| 2018/0000443 A1 * | 1/2018 | Matsuura | A61B 6/4405 | |
| 2018/0014396 A1 * | 1/2018 | Imamura | H05G 1/265 | |
| 2018/0035524 A1 * | 2/2018 | Matsuura | A61B 6/56 | |

FOREIGN PATENT DOCUMENTS

| | | |
|---|---|---|
| JP | 2005-160664 | 6/2005 |
| JP | 2013-512065 | 4/2013 |
| JP | 2014-195590 | 10/2014 |

OTHER PUBLICATIONS

"Written Opinion (Form PCT/ISA/237)", dated Feb. 7, 2017, with English translation thereof, pp. 1-6.

* cited by examiner

RADIATION IRRADIATION DEVICE

CROSS-REFERENCE TO RELATED APPLICATIONS

This application is a Continuation of PCT International Application No. PCT/JP2016/083450 filed on Nov. 11, 2016, which claims priority under 35 U.S.C § 119(a) to Japanese Patent Application No. 2015-230363 filed on Nov. 26, 2015 and Japanese Patent Application No. 2016-079680 filed on Apr. 12, 2016. Each of the above application(s) is hereby expressly incorporated by reference, in its entirety, into the present application.

BACKGROUND OF THE INVENTION

1. Field of the Invention

The present invention relates to a radiation irradiation device having an arm part provided with a radiation source.

2. Description of the Related Art

In the related art, portable radiation irradiation devices used in a case where a patient's radiographic image is captured in operating rooms, examination rooms, or patients rooms have been suggested variously (refer to JP2005-160664A, JP2013-512065A, and JP2014-195590A).

The portable radiation irradiation devices basically include a leg part enabled to travel by wheels, a body part that houses a control unit including a battery for driving a radiation source, an electric circuit related to the driving of the radiation source, and the like and is held on the leg part, and an arm part connected to the body part, and are configured by attaching the radiation source to a tip of the arm part.

In a case where such radiation irradiation devices are used, a radiation irradiation device is first moved to the vicinity of a patient's bed. Next, the radiation source is moved to a desired position, and a radiation detector is moved to a desired position behind a subject. In this state, the subject is irradiated with radiation by driving the radiation source, and a radiographic image of the subject is acquired by detecting the radiation transmitted through the subject using the radiation detector.

Here, various kinds of equipment other than a portable radiation irradiation device are disposed in operating rooms or examination rooms where the radiation irradiation device is used, and wiring lines to be connected to the equipment are present on the floors in the rooms. Therefore, it is better that the radiation irradiation device is as small as possible. Additionally, even in patients rooms, beds are disposed at narrow intervals, or there are visitors for visiting or the like. Thus, it is better that the radiation irradiation device is also as smaller as possible.

Thus, it is suggested that casters in which rotating shafts of wheels revolve are attached to the leg part, and the revolvability of the entire device is improved.

SUMMARY OF THE INVENTION

However, for example, in a case where the casters are provided as front wheels and rear wheels of the radiation irradiation device, straight traveling stability decreases in a case where the rear wheels are revolvable during the movement of the device. Hence, for example, in a case where the device is moved in a hurry in an emergency, cautions are required.

An object of the invention is to provide a radiation irradiation device capable of ensuring the straight traveling stability of rear wheels while maintaining the revolvability of front wheels, in view of the above problems.

A radiation irradiation device of the invention comprises a radiation generation unit that generates radiation; an arm part having one end to which the radiation generation unit is attached; a support member having one end to which the other end of the arm part is connected so as to be rotationally movable; a body part to which the other end of the support member is connected; and a leg part on which the body part is placed. In a case where a side toward which the arm part extends from the body part during use of the device is defined as a front side, the leg part includes a first caster which is provided on the front side of a bottom surface of the leg part and to which a rotating shaft of a wheel is revolvably supported and a second caster which is provided on a rear side of the bottom surface of the leg part and to which a rotating shaft of a wheel is revolvably supported. A diameter of the wheel of the second caster and is greater than a diameter of the wheel of the first caster, and a gravity center position of the entire device is closer to the second caster side than a center between the first caster and the second caster in a state where the arm part is rotationally moved until the radiation generation unit is located at a vertically lowermost position.

Additionally, in the radiation irradiation device of the above invention, it is desirable that a revolution resistance of the second caster is twice or more a revolution resistance of the first caster.

Additionally, the radiation irradiation device of the invention may further comprise a switching unit that performs switching of the rotating shaft of the wheel of the second caster between a revolvable state and a non-revolvable state.

Additionally, in the radiation irradiation device of the above invention, it is preferable that the arm part is connected to the support member so as to be rotationally movable only around one axis extending in a right and left direction.

Additionally, in the radiation irradiation device of the invention, it is preferable that the other end of the support member is non-rotatably fixed to the body part.

Additionally, in the radiation irradiation device of the above invention, the arm part is not capable of being extendable and retractable.

Additionally, in the radiation irradiation device of the above invention, it is preferable that an inclination of an extension direction of the support member with respect to a vertical direction is 10 degrees or more and 30 degrees or less.

Additionally, in the radiation irradiation device of the above invention, it is preferable that the leg part has a V-shaped foot arm part that widens in a right and left direction toward the front, and bottom surfaces of two front tip parts of the foot arm part may be respectively provided with the first casters.

Additionally, in the radiation irradiation device of the above invention, it is preferable that a thickness of the front two tip parts of the foot arm part in the vertical direction is smaller than a thickness of a V-shaped root part of the foot arm part in the vertical direction.

Additionally, in the radiation irradiation device, it is preferable that a width of each of the front tip parts of the foot arm part is smaller than a width of a connecting part of each of the legs connected to a root part that widens in a right and left direction in the foot arm part.

Additionally, it is preferable that the radiation irradiation device of the above invention is configured separately from a radiation detector that detects radiation that is generated from the radiation generation unit and is transmitted through a subject.

Additionally, in the radiation irradiation device of the above invention, the body part may include a charging part that charges the radiation detector.

According to the radiation irradiation device of the invention, the diameter of the wheel of the second caster provided as a rear wheel is made larger than the diameter of the wheel of the first caster provided as a front wheel, and the gravity center position of the entire device is configured to become the second caster side in a state where the arm part is rotationally moved until the radiation generation unit is located at the vertically lowermost position. Thus, the revolution resistance the second caster can be increased. Accordingly, the straight traveling stability of the rear wheel can be secured while maintaining the revolvability of the front wheel.

DESCRIPTION OF THE PREFERRED EMBODIMENTS

Figure 1:
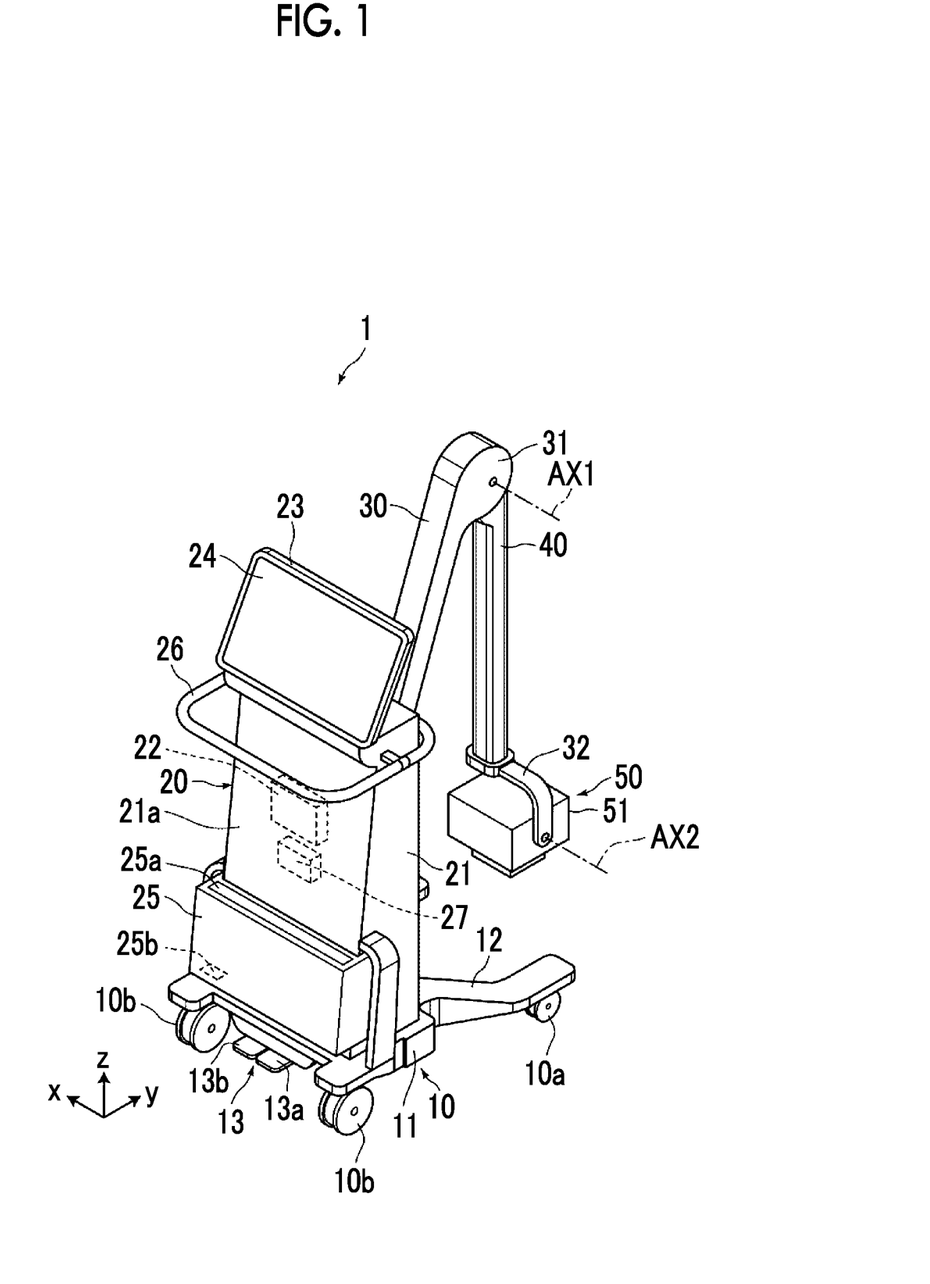
FIG. 1 is a perspective view illustrating an entire shape of a radiation irradiation device of an embodiment of the invention.
Figure 2:
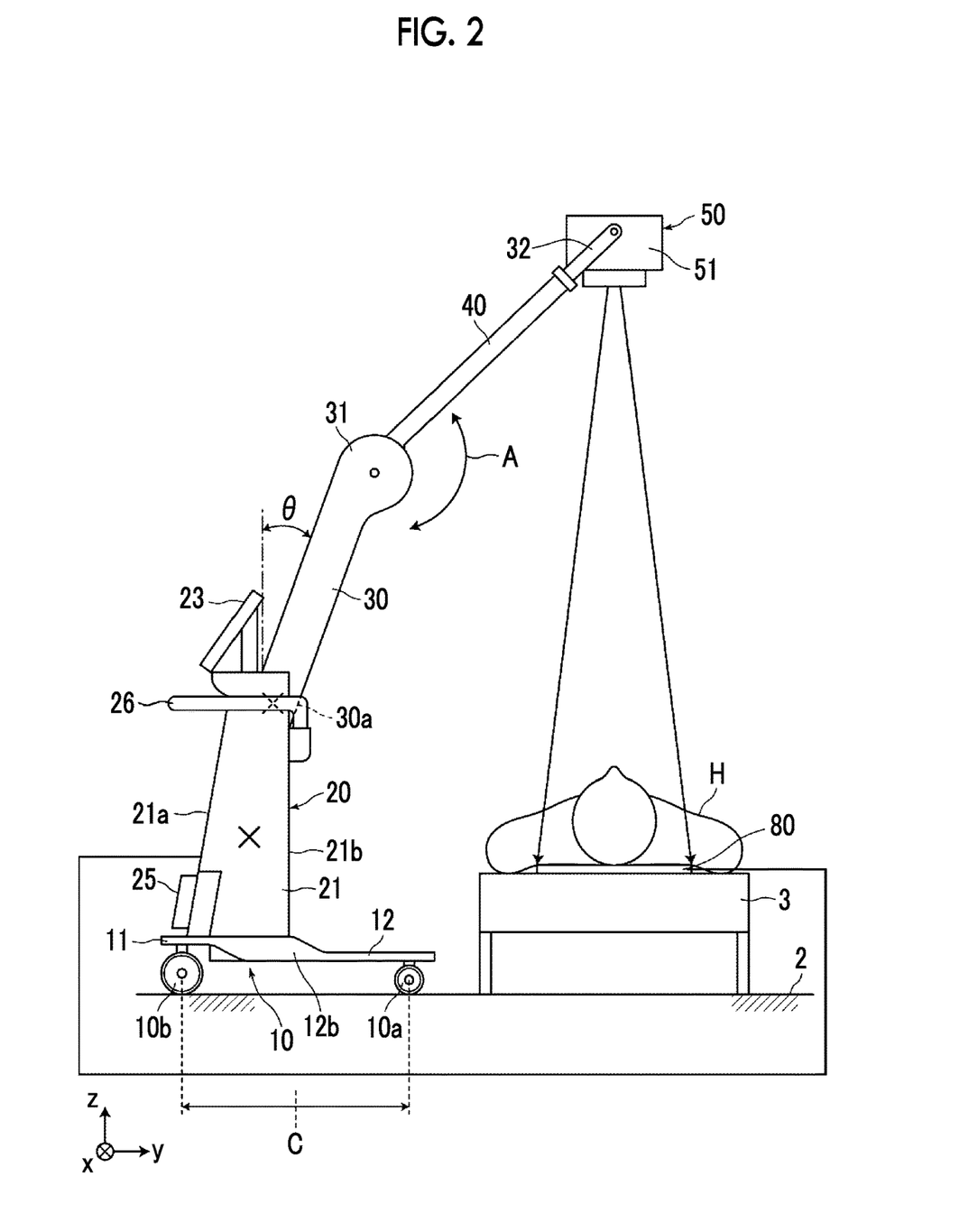
FIG. 2 is a view illustrating the state of the radiation irradiation device of the embodiment of the invention in a case where the device is used.

Hereinafter, a radiation irradiation device of an embodiment of the invention will be described in detail, referring to the drawings. FIG. 1 is a perspective view illustrating the entire shape of the radiation irradiation device of the present embodiment in a case where the device is not used, and FIG. 2 is a side view illustrating the state of the radiation irradiation device of the present embodiment in a case where the device is used. In addition, in the following, an upper side and a lower side in the vertical direction in a state where the radiation irradiation device is placed, for example, a device placement surface, such as a floor of a medical institution, are referred to as "up" and "down", respectively, and a direction perpendicular to the vertical direction in the same state is referred to as a "horizontal" direction. Additionally, in the views to be described below, the vertical direction is defined as a z direction, a right and left direction of the radiation irradiation device is defined as an x direction, and a forward-backward direction of the radiation irradiation device is defined as a y direction. In addition, the front herein means a side toward which an arm part 40 is extended from a body part of the radiation irradiation device in a case where the device is used.

As illustrated in FIGS. 1 and 2, a radiation irradiation device 1 of the present embodiment includes a leg part 10, a body part 20, a support member 30, an arm part 40, and a radiation generation unit 50.

Figure 3:
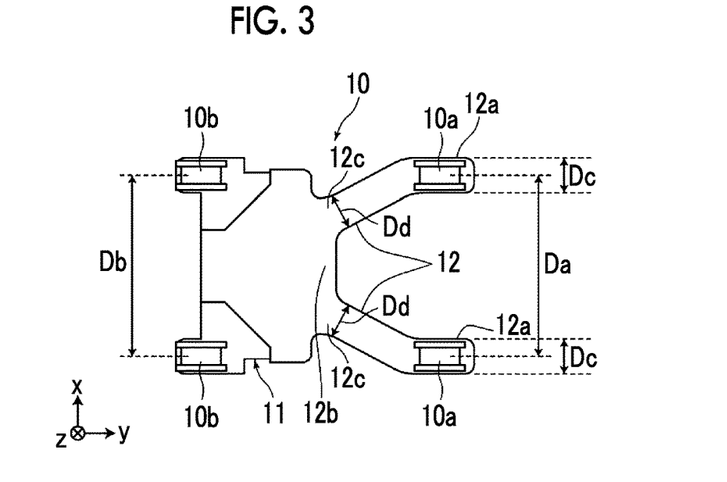
FIG. 3 is a view of a leg part as seen from below.

The leg part 10 is capable of traveling on a device placement surface 2, and includes a plate-shaped pedestal part 11 on which the body part 20 is placed, and a foot arm part 12 that extends from the pedestal part 11 toward the front. FIG. 3 is a view of the leg part 10 as seen from below. As illustrated in FIG. 3, the foot arm part 12 is formed in a V shape that widens in the right and left direction toward the front. First casters 10a are respectively provided on bottom surfaces of two tip parts 12a at the front of the foot arm part 12, and second casters 10b are respectively provided on bottom surfaces of two corners at the rear of the pedestal part 11. By forming the foot arm part 12 in a V shape as described above, for example, as compared to a case where the entire leg part 10 is formed in a rectangular shape, an edge part of the leg part does not easily collide against its surrounding obstacle in a case where the leg part 10 is rotated. Thus, handling can be made easy. Additionally, weight reduction can also be achieved.

Additionally, as illustrated in FIG. 2, the foot arm part 12 is formed such that the thickness of the two front tip parts in the vertical direction is smaller than the thickness of a V-shaped root part 12b in the vertical direction. In this way, by making the thickness of the two front tip parts 12a of the foot arm part 12 small, it is possible to make the two tip parts 12a easier to enter a location under a bed where a subject is sleeping, or the like, and it is possible to use the device in a narrower space. In addition, the V-shaped root part means a portion where the legs that widen in the right and left direction toward the front join together at the rear side.

Figure 4A:
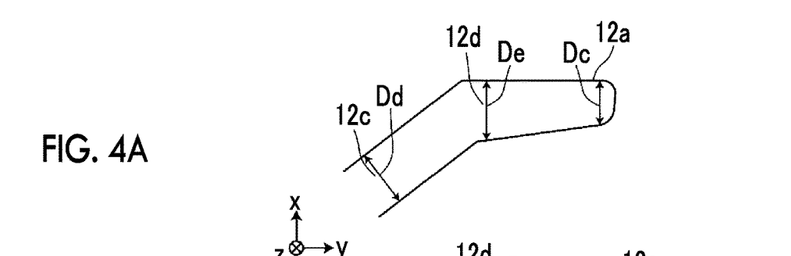
FIGS. 4A, 4B, and 4C are views illustrating modification examples of the leg part.
Figure 4B:
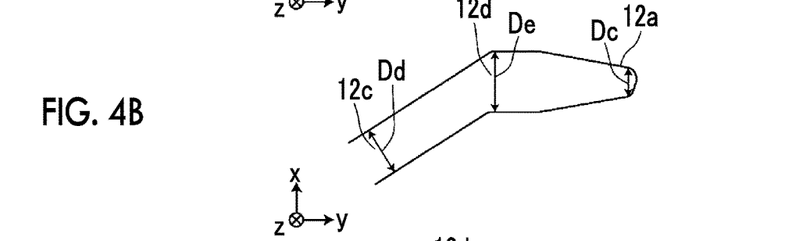
Figure 4C:
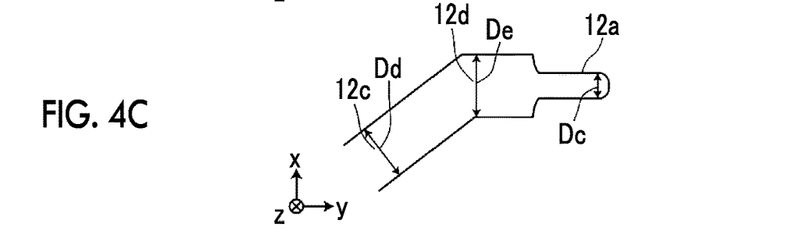

Additionally, in the present embodiment, as illustrated in FIG. 3, a width Dc of the respective front tip parts 12a of the foot arm part 12, and a width Dd of the connecting parts 12c of two legs connected to the root part 12b are made to have the same width. However, as illustrated in FIGS. 4A to 4C, it is desirable to make the width Dc of the tip parts 12a narrower than the width Dd of the connecting parts 12c. By configuring the invention in this way, the respective tip parts 12a of the foot arm part 12 can be easily inserted under the bed.

Additionally, as illustrated in FIG. 3 and FIGS. 4A to 4C, in a case where the two legs of the foot arm part 12 are constituted of portions that widen gradually in the right and left direction (x direction) toward the front, and portions that extend parallel to each other in the forward-backward direction (y direction), as illustrated in FIGS. 4A to 4C, it is preferable that the width Dc of the tip parts 12a is narrower than the width De of base end parts 12d of the portions that extend parallel to each other. Additionally, illustrated in FIGS. 4B and 4C, the width Dd of the connecting parts 12c connected to the root part 12b and the width De of the base end parts 12d of the portions that extend parallel to each other may be made the same. In addition, the width Dc, the width Dd, and the width De herein are widths in directions orthogonal to directions in which the legs of the foot arm part 12 extend, in the horizontal direction. Additionally, it is desirable to give curvature to corners of the tip parts 12a. By configuring the invention in this way, a pain in a case where the tip parts 12a bump into a user can be mitigated.

Each first caster 10a has a shaft that extends in the upward-downward direction, and is attached to a bottom surface of the foot arm part 12 such that a rotating shaft of a wheel is revolvable within a horizontal plane about the shaft of the first caster. Additionally, each second caster 10b also has a shaft that extends in the upward-downward direction, and is attached to a bottom surface of the pedestal part 11 such that a rotating shaft of a wheel is revolvable within the horizontal plane about the shaft of the second caster. In addition, the rotating shaft of each wheel herein is a rotating shaft in a case where the wheel rotates and travels. The leg part 10 is configured so as to be capable of traveling in a certain direction on the device placement surface 2 by the first casters 10*a* and the second casters 10*b*.

As illustrated in FIGS. 1 and 2, the first casters 10*a* and the second casters 10*b* are configured such that the diameter of a wheel of each rear second caster 10*b* becomes greater than the diameter of a wheel of each front first caster 10*a*. By configuring the invention in this way, the ground contact area of the wheels of the second casters 10*b* can be made greater than the ground contact area of the wheels of the first casters 10*a*, and the revolution resistance of the second casters 10*b* can be made greater than the revolution resistance of the first casters 10*a*. This can make it difficult for the second casters 10*b* to revolve during the transport of the radiation irradiation device 1, and straight traveling stability of traveling of the radiation irradiation device 1 can be improved.

In addition, as illustrated in FIG. 3, in the present embodiment, a width Da between the two wheels of the first caster 10*a* and a width Db between the two wheels of the second caster 10*b* are configured to become the same width. However, the invention is not limited to this, the width Db may be configured to be greater than the width Da. According, since the gravity center position of the entire radiation irradiation device 1 can be made closer to the rear side, the radiation irradiation device 1 can be made it difficult to fall forward due to the weight of the radiation generation unit 50 or the like. Additionally, the width Da may be configured to be greater than the width Db. Accordingly, the instability of the radiation irradiation device 1 in the right and left direction due to the weight of the radiation generation unit 50 in a case where the arm part 40 to be described below is extended can be suppressed.

Additionally, as illustrated in FIG. 1, a pedal part 13 is provided at the rear of the leg part 10. The pedal part 13 is constituted of two pedals of a first pedal 13*a* and a second pedal 13*b*. The first pedal 13*a* is a pedal for bringing the second casters 10*b* into a non-revolvable state. As a user steps on the first pedal 13*a*, the second casters 10*b* are configured so as to be locked in revolution by a locking mechanism and brought into the non-revolvable state.

Additionally, the second pedal 13*b* is a pedal for bringing the second casters 10*b* into a revolvable state from the non-revolvable state. As the user steps on the second pedal 13*b*, the second casters 10*b* are configured so as to be released from the locking by the locking mechanism and brought into the revolvable state again.

A well-known configuration can be used as the locking mechanism that locks the revolution of the second casters 10*b*. For example, the revolution may be locked such that both sides of the wheels of the second casters 10*b* are sandwiched by plate-shaped members, or the revolution may be locked by providing members that stop the rotation of shafts of the second casters 10*b* that extend in the upward-downward direction. In addition, the pedal part 13 and the locking mechanism in the present embodiment are equivalent to a switching unit.

In the radiation irradiation device 1 of the present embodiment, the straight traveling stability of traveling of the radiation irradiation device 1 can be guaranteed to some extent by making the revolution resistance of the second caster 10*b* greater than the revolution resistance of the first casters 10*a*. However, the revolution of the second casters 10*b* may be locked as the user steps on the above-described first pedal 13*a*, for example, in a case where it is necessary to more reliably make the device travel straight.

The body part 20 is placed on the pedestal part 11 of the leg part 10, and includes a housing 21. A control unit 22 that controls driving of the radiation irradiation device 1 and a charging part 27 are housed within the housing 21.

The control unit 22 performs control regarding generation of radiation and irradiation with radiation, such as a tube current, irradiation time, and a tube voltage, in the radiation generation unit 50, and control regarding acquisition of radiographic images, such as image processing of a radiographic image acquired by a radiation detector to be described below. The control unit 22 is configured of, for example, a computer in which a program for control is installed, exclusive hardware, or a combination of both.

Figure 5:
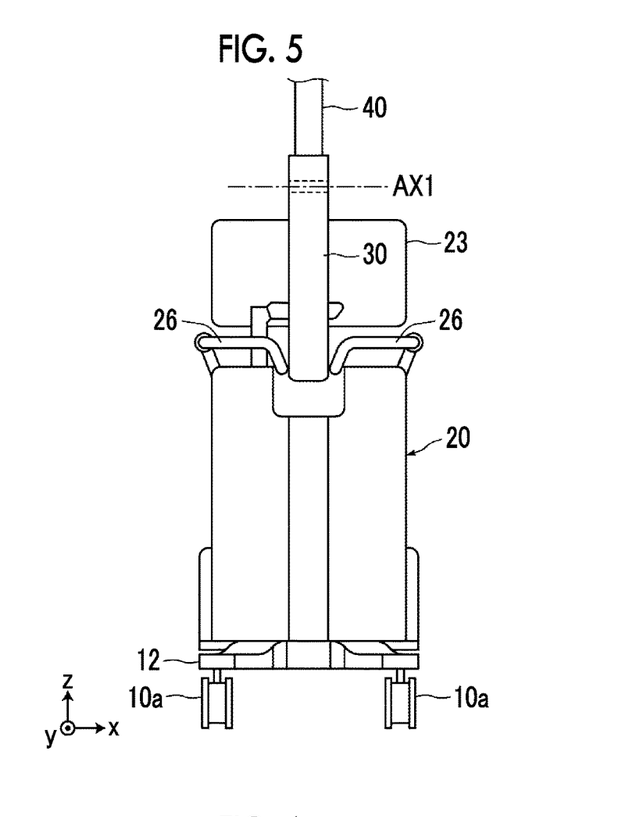
FIG. 5 is a view of the radiation irradiation device illustrated in FIG. 1 as seen from the front.

Additionally, the monitor 23 is attached to an upper surface of the housing 21. Additionally, a handle part 26 for pushing or pulling the radiation irradiation device 1 is attached to an upper part of the housing 21. The handle part 26 is provided so as to go around the housing 21, and is configured so as to be capable of being held not only from a rear side of the radiation irradiation device 1 but also from a front side or a lateral side. FIG. 5 is a view of the radiation irradiation device 1 as seen from the front. As illustrated in FIG. 5, the handle part 26 is provided so as to go round to a front side of the body part 20.

Additionally, the body part 20 is configured to be capable of housing the radiation detector to be described below on the surface thereof opposite to a side where the support member 30 is attached. A configuration in which the radiation detector is housed will be described below.

The monitor 23 made of a liquid crystal panel or the like, and displays a radiographic image acquired by imaging of a subject, and various kinds of information required for the control of the radiation irradiation device 1. Additionally, the monitor 23 includes a touch panel type input unit 24, and receives input of various instructions required for the operation of the radiation irradiation device 1. Specifically, input for setting of imaging conditions and input for imaging, that is, emission of radiation, is received. The monitor 23 is attached to the upper surface of the housing 21 so as to be capable of changing the inclination and the rotational movement position of a display surface with respect to the horizontal direction. Additionally, instead of the touch panel type input unit 24, buttons for performing various operations may be included as the input unit.

The radiation generation unit 50 is configured such that a radiation source, a collimator for narrowing the irradiation range of radiation, and the like is housed within a housing 51. The radiation source is constituted of, for example, an X-ray tube, a booster circuit, and cooling means for cooling the X-ray tube, and the like. Emission of the radiation from the radiation source of the radiation generation unit 50 is performed depending on an instruction from an input unit 24 in the monitor 23 by an operator.

An L-shaped radiation source attachment part 32 is provided at a tip (one end) of the arm part 40. The radiation generation unit 50 is attached to the one end of the arm part 40 via the radiation source attachment part 32. The radiation generation unit 50 is connected to the radiation source attachment part 32 so as to be rotationally movable with an axis AX2 as a rotational movement axis. The rotational movement axis AX2 is an axis that extends in the right and left direction (x direction). In addition, the radiation source attachment part 32 holds the radiation generation unit 50 such that the radiation generation unit 50 moves rotationally via a friction mechanism. For this reason, the radiation generation unit 50 is rotationally movable by applying a certain degree of strong external force, and maintains a relative angle with respect to the arm part 40 without moving rotationally unless an external force is applied.

One end of the support member 30 is connected to the other end of the arm part 40. The arm part 40 is connected to the support member 30 so as to be rotationally movable with an axis AX1 as a rotational movement axis. The rotational movement axis AX1 is an axis that extends in the right and left direction (x direction). The arm part 40 moves rotationally in a direction of arrow A illustrated in FIG. 2 such that an angle formed with the support member 30 is changed about the rotational movement axis AX1. That is, the arm part 40 is capable of moving rotationally only around one axis (the rotational movement axis AX1) that extends in the right and left direction. In the present embodiment, as described above, the orientation of the arm part 40 can be freely changed by the revolution of the first casters 10a and the second casters 10b. Thus, the degree of freedom of rotation of the arm part 40 can be lowered, and a simpler configuration can be adopted.

A rotational movement part 31 having the rotational movement axis AX1 holds the arm part 40 such that the arm part 40 moves rotationally via the friction mechanism. For this reason, the arm part 40 is rotationally movable by applying a certain degree of strong external force, and maintains a relative angle with respect to the support member 30 without moving rotationally unless an external force is not applied.

In addition, the arm part 40 does not have an extendable and retractable configuration, and is configured to be incapable of being extended and retracted. In the present embodiment, as described above, the orientation of the arm part 40 can be freely changed together with the body part 20 by the revolution of the first casters 10a and the second casters 10b. Thus, it is not necessary to provide a configuration in which the arm part 40 is extended and retracted, and a simpler configuration can be adopted. However, the invention is not limited to such a configuration and a configuration in which the arm part 40 is extendable and retractable may be adopted.

Additionally, the arm part 40 is configured so as not to move rotationally to the rear side rather than the vertical direction. Accordingly the radiation irradiation device 1 can be prevented from falling toward the rear side.

In addition, although the rotational movement of the arm part 40 and the radiation generation unit 50 is performed via the friction mechanism, rotational movement positions of these parts may be fixed by a well-known locking mechanism. In this case, the rotational movement of the arm part 40 and the radiation generation unit 50 becomes possible by releasing the locking mechanism. The rotational movement positions can be fixed by locking the locking mechanism at desired rotational movement positions.

The other end of the support member 30 is connected to the surface of the body part 20 on the front side. The support member 30 is provided so as to be fixed with respect to the body part 20, and is attached so as to be non-rotatable with respect to the body part 20. In the present embodiment, as described above, the orientation of the arm part 40 can be freely changed together with the body part 20 by the revolution of the first casters 10a and the second casters 10b. Thus, it is not necessary to make the support member 30 have a degree of freedom, and a simpler configuration can be adopted. However, the invention is not limited to this, and the support member 30 may be configured to rotate with emphasis on handleability. That is, the support member 30 may be configured so as to be rotatable with an axis passing through the center of the connecting portion of the support member 30 to the body part 20 and extending in the vertical direction as a rotational axis.

As illustrated in FIG. 2, the support member 30 of the present embodiment is provided such that the inclination θ of the extension direction thereof with respect to the vertical direction becomes 10 degrees or more and 30 degrees or less. By setting the inclination θ of the support member 30 to 10 degrees or more, the user's front visibility can be secured. Additionally, by setting the inclination θ of the support member 30 to 30 degrees or less, the arm part 40 can be folded downward and the radiation generation unit 50 can be housed. Additionally, in a case where the radiation irradiation device 1 is used, a source image receptor distance (SID) can be secured.

In addition, the extension direction of the support member 30 means an axial direction thereof in a case where the support member 30 is formed linearly. Additionally, the extension direction means a direction in which a straight line connecting centers of both end parts of the support member 30 together extends in a case where the support member 30 is formed in shapes, such as an arc, other than the straight line.

Additionally, as illustrated in FIG. 2, the center (illustrated by dotted line mark x in FIG. 2) of a connection portion between the support member 30 and the body part 20 is configured to be located rearward of a center position C between the rotating shafts of the wheels of the first casters 10a and the rotating shafts of the wheels of the second casters 10b. Since the gravity center position of the entire radiation irradiation device 1 can be brought closer to the rear side by configuring the invention in this way, the radiation irradiation device 1 can be prevented from falling forward due to the weight of the support member 30, the arm part 40, and the radiation generation unit 50. Additionally, the center of the connection portion between the support member 30 and the body part 20 is configured to be located forward of the rotating shafts of the wheels of the second casters 10b. By configuring the invention in this way, the device does not easily fall rearward either.

Additionally, it is desirable that the position of the front surface 21b of the housing 21 of the body part 20 is rearward of or the same as the position of a front surface 30a of the connection portion between the support member 30 and the body part 20. Since the gravity center position can be brought closer to the rear side by configuring the invention in this way, the device can be made it difficult to fall forward.

Additionally, as illustrated in FIG. 2, the surface of the body part 20 on the front side and the connection portion between the body part 20 and the support member 30 are the same positions in the forward-backward direction. Thus, the gravity center position of the radiation irradiation device 1 can be brought closer to the rear side, and the device can be made it difficult to fall forward.

Additionally, as illustrated in FIG. 2, the monitor 23 is connected to a location closer to the rear side than the center of the connection portion between the support member 30 and the body part 20. By configuring the invention in this way, it is possible to make the monitor 23 easier to view.

Here, in a case where the radiation irradiation device 1 illustrated in FIG. 1 is not used, a state where the arm part 40 is rotationally moved until the radiation generation unit 50 is located at vertically lowermost position is brought about. In this state, the entire radiation irradiation device 1 is configured such that the gravity center position of the radiation irradiation device 1 is closer to the second casters 10b side than the center between first caster 10a and the second caster 10b.

In addition, the gravity center position of the radiation irradiation device 1 being closer to the second casters 10b side than the center between the first casters 10a and the second casters 10b means that the gravity center position of the radiation irradiation device 1 is present closer to the second casters 10b side than the center between the first casters 10a and the second casters 10b within a three-dimensional space including the entire radiation irradiation device 1. That is, the height of the gravity center position is not necessarily limited to a height on a straight line connecting each first caster 10a and each second caster 10b together.

The gravity center position of the radiation irradiation device 1 of the present embodiment is the position of a solid line mark x of FIG. 2 in a state where the arm part 40 is rotationally moved until the radiation generation unit 50 is located at the vertically lowermost position in FIG. 2.

By setting the gravity center position of the radiation irradiation device 1 to the second casters 10b side in this way, the revolution resistance of the second casters 10b can be made greater than the revolution resistance of the first casters 10a. This can make it difficult for the second casters 10b to revolve during the transport of the radiation irradiation device 1, and straight traveling stability of traveling of the radiation irradiation device 1 can be improved. It is desirable that the revolution resistance the second casters 10b is twice or more the revolution resistance of the first casters 10a.

In addition, in the radiation irradiation device 1 of the present embodiment, in a case where the revolution resistance of the first casters 10a and the revolution resistance of the second casters 10b were measured 4 times, respectively, assuming the diameter of the wheels of the first casters 10a is 0.05 m, and the diameter of the wheels of the second casters 10b is 0.065 m, the average of the revolution torques of the first casters 10a is 0.28 N·m, and the average of the revolution torque of the second casters 10b is 0.87 N·m. In this case, it was confirmed that the straight traveling stability of the traveling of the radiation irradiation device 1 is excellent.

In the present embodiment, in a case where the subject is imaged, as illustrated in FIG. 2, the imaging is performed by disposing a radiation detector 80 under a subject H that lies on ones' back on a bed 3 and radiating the radiation (for example, X rays) emitted from the radiation generation unit 50 to the subject H through the radiation detector 80. In addition, the radiation detector 80 and the radiation irradiation device 1 are connected together with or without wires. Accordingly, the radiographic image of the subject H acquired by the radiation detector 80 is directly input to the radiation irradiation device 1.

Figure 6:
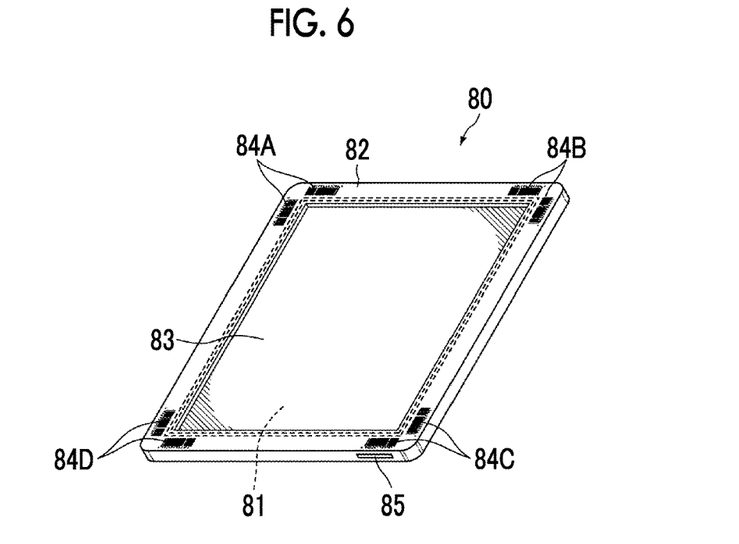
FIG. 6 is an external perspective view of a radiation detector as seen from a front surface that is a radiation detection surface side.

Here, the radiation detector 80 will be briefly described with reference to FIG. 6. FIG. 6 is an external perspective view of the radiation detector as seen from a front surface that is a radiation detection surface side. As illustrated in FIG. 6, the radiation detector 80 is a cassette type radiation detector including a housing 82 that has a rectangular flat plate shape and houses a detecting part 81. The detecting part 81 includes a scintillator (fluorescent body) that converts incident radiation into visible light as is well known, and a thin film transistor (TFT) active matrix substrate. A rectangular imaging region where a plurality of pixels that accumulate electrical charge according to the visible light from the scintillator are arrayed is formed on the TFT active matrix substrate.

Additionally, the housing 82 includes a round-chamfered metallic frame, and an imaging control unit including a gate driver that gives a gate pulse to a gate of a TFT to switch the TFT, a signal processing circuit that converts an electrical charge accumulated in a pixel into an analog electrical signal representing an X-ray image to output the converted signal, and the like in addition to the detecting part 81 is built in the housing. Additionally, the housing 82 has, for example, a size based on International Organization for Standardization (ISO) 4090:2001 that is substantially the same as a film cassette, an imaging plate (IP) cassette, and a computed radiography (CR) cassette.

A transmission plate 83 that allows radiation to be transmitted therethrough is attached to a front surface of the housing 82. The transmission plate 83 has a size that substantially coincides with a detection region of radiation in the radiation detector 80, and is formed of a carbon material that is lightweight, has high stiffness, and has high radiation transparency. In addition, the shape of the detection region is the same oblong shape as the shape of the front surface of the housing 82. Additionally, the portion of the frame of the housing 82 protrudes from the transmission plate 83 in a thickness direction of the radiation detector 80. For this reason, the transmission plate 83 is not easily damaged.

Markers 84A to 84D showing identification information for identifying the radiation detector 80 are applied to four corners of the front surface of the housing 82. In the present embodiment, the markers 84A to 84D consist of two bar codes that are orthogonal to each other, respectively.

Additionally, a connector 85 for charging the radiation detector 80 is attached to a side surface of the housing 82 on the markers 84C, 84D side.

In a case where the radiation irradiation device 1 according to the present embodiment is used, the operator rotationally moves the arm part 40 around the rotational movement axis AX1 in an illustrated counterclockwise direction from an initial position of the arm part 40 illustrated in FIG. 1, and thereby the radiation generation unit 50 is moved to a target position immediately above the subject H, as illustrated in FIG. 2. The radiographic image of the subject H can be acquired by driving the radiation generation unit 50 according to an instruction from the input unit 24 to irradiate the subject H with radiation and detecting the radiation transmitted through the subject H, using the radiation detector 80, after the radiation generation unit 50 is moved to the target position.

In addition, as the radiation detector 80, as described above, it is desirable to use a radiation detector in which the TFT active matrix substrate including the scintillator and light-receiving elements are laminated and which receives irradiation of radiation from a TFT active matrix substrate side (a side opposite to a scintillator side). By using such a high-sensitivity radiation detector 80, a low-output radiation source can be used as the radiation generation unit 50, and the weight of the radiation generation unit 50 can be made light. In addition, generally, the radiation source output of the radiation generation unit 50 and the weight of the radiation generation unit 50 are in a proportional relation.

Since the weight of the radiation generation unit 50 can be made light as described above, the total weight of the radiation irradiation device 1 can also be made light. Accordingly, by using the revolving casters as the second casters 10b (rear wheels) as in the radiation irradiation device 1 of the present embodiment, the revolution performance of the radiation irradiation device 1 can be improved, and handling can be markedly improved.

In addition, the radiation source output of the radiation generation unit 50 is preferably 4 kW or less, and is more preferably 2.5 kW or less. Additionally, the total weight of radiation irradiation device 1 is preferably 120 kg or less, and is more preferably 90 kg or less.

Next, a configuration in which the radiation detector 80 in the body part 20 is capable of being housed will be described. As illustrated in FIGS. 1 and 2, the housing 21 of the body part 20 has a flat surface 21*a* inclined to the support member 30 side, on a surface opposite to a side where the support member 30 is attached, and the flat surface 21*a* is provided with the is provided with a cradle 25.

An insertion port 25*a* for inserting the radiation detector 80 is formed in an upper surface of the cradle 25. The insertion port 25*a* has an elongated shape of a size such that the radiation detector 80 is fitted thereto. In the present embodiment, one end part of the radiation detector 80 on a side having the connector 85 is inserted into the insertion port 25*a*. Accordingly, this one end part is supported by the cradle 25, and the radiation detector 80 is held by the cradle 25. In this case, a front surface of the radiation detector 80 is directed to the flat surface 21*a* side. In a case where the one end part of the radiation detector 80 is supported by the cradle 25, the one end part of the radiation detector 80 is located on a vertically lower side, and the other opposite end part facing the one end part is located on a vertically upper side.

A connector 25*b* is attached to a bottom part of the cradle 25. The connector 25*b* is electrically connected to the connector 85 of the radiation detector 80 in a case where the radiation detector 80 is held by the cradle 25. The connector 25*b* is electrically connected to the charging part 27. The charging part 27 includes a battery, and charges the radiation detector 80 via the connector 25*b*. In addition, the charging part 27 is connected to an external power source via a connector (not illustrated), and the battery is charged under the supply of electrical power from the external power source.

The cradle 25 is provided on the flat surface 21*a* on the rear side of the body part 20 as described above, and is disposed below half of the height of the body part 20 in the vertical direction. Since the gravity center position of the entire radiation irradiation device 1 can be brought closer to the rear side by configuring the invention in this way, the radiation irradiation device 1 can be prevented from falling forward due to the weight of the support member 30, the arm part 40, and the radiation generation unit 50. Additionally, a bag, such as a protective cover, is easily put on an exposed end part of the radiation detector 80 inserted into the cradle 25.

Additionally, although radiation detectors 80 having various sizes are insertable into the cradle 25, particularly, radiation detectors 80 having a mini size of 17 inches×17 inches, and 14 inches×17 inches are insertable.

EXPLANATION OF REFERENCES

1: radiation irradiation device
3: bed
10: leg part
10*a*: first caster
10*b*: second caster
11: pedestal part
12: foot arm part
12*a*: tip part
12*b*: root part
13: pedal part
13*a*: first pedal
13*b*: second pedal
20: body part
21: housing
22: control unit
23: monitor
24: input unit
25: cradle
25*a*: insertion port
25*b*: connector
26: handle part
27: charging part
30: support member
31: rotational movement part
32: radiation source attachment part
40: arm part
50: radiation generation unit
51: housing
80: radiation detector
81: detecting part
82: housing
83: transmission plate
85: connector

What is claimed is:

1. A radiation irradiation device comprising:
   a radiation generation unit that generates radiation;
   an arm part having one end to which the radiation generation unit is attached;
   a support member having one end to which the other end of the arm part is connected so as to be rotationally movable;
   a body part to which the other end of the support member is connected; and
   a leg part on which the body part is placed,
   wherein in a case where a side toward which the arm part extends from the body part during use of the device is defined as a front side, the leg part includes a first caster which is provided on the front side of a bottom surface of the leg part and to which a rotating shaft of a wheel is revolvably supported and a second caster which is provided on a rear side of the bottom surface of the leg part and to which a rotating shaft of a wheel is revolvably supported, and
   wherein a diameter of the wheel of the second caster is greater than a diameter of the wheel of the first caster, and a gravity center position of the entire device is closer to the second caster side than a center between the first caster and the second caster in a state where the arm part is rotationally moved until the radiation generation unit is located at a vertically lowermost position.

2. The radiation irradiation device according to claim 1, wherein a revolution resistance of the second caster is twice or more a revolution resistance of the first caster.

3. The radiation irradiation device according to claim 1, further comprising:
   a switching unit that performs switching of the rotating shaft of the wheel of the second caster between a revolvable state and a non-revolvable state.

4. The radiation irradiation device according to claim 2, further comprising:
   a switching unit that performs switching of the rotating shaft of the wheel of the second caster between a revolvable state and a non-revolvable state.

5. The radiation irradiation device according to claim 1, wherein the arm part is connected to the support member so as to be rotationally movable only around one axis extending in a right and left direction.

6. The radiation irradiation device according to claim 2, wherein the arm part is connected to the support member so as to be rotationally movable only around one axis extending in a right and left direction.

7. The radiation irradiation device according to claim 3, wherein the arm part is connected to the support member so as to be rotationally movable only around one axis extending in a right and left direction.

8. The radiation irradiation device according to claim 4, wherein the arm part is connected to the support member so as to be rotationally movable only around one axis extending in a right and left direction.

9. The radiation irradiation device according to claim 1, wherein the other end of the support member is non-rotatably fixed to the body part.

10. The radiation irradiation device according to claim 2, wherein the other end of the support member is non-rotatably fixed to the body part.

11. The radiation irradiation device according to claim 3, wherein the other end of the support member is non-rotatably fixed to the body part.

12. The radiation irradiation device according to claim 4, wherein the other end of the support member is non-rotatably fixed to the body part.

13. The radiation irradiation device according to claim 5, wherein the other end of the support member is non-rotatably fixed to the body part.

14. The radiation irradiation device according to claim 1, wherein the arm part is not capable of being extendable and retractable.

15. The radiation irradiation device according to claim 1, wherein an inclination of an extension direction of the support member with respect to a vertical direction is 10 degrees or more and 30 degrees or less.

16. The radiation irradiation device according to claim 1, wherein the leg part has a V-shaped foot arm part that widens in a right and left direction toward the front, and bottom surfaces of two front tip parts of the foot arm part are respectively provided with the first casters.

17. The radiation irradiation device according to claim 16, wherein a thickness of the front two tip parts of the foot arm part in the vertical direction is smaller than a thickness of a root part of the foot arm part in the vertical direction.

18. The radiation irradiation device according to claim 16, wherein a width of each of the front tip parts of the foot arm part is smaller than a width of a connecting part of each of the legs connected to a root part that widens in a right and left direction in the foot arm part.

19. The radiation irradiation device according to claim 1, wherein the radiation irradiation device is configured separately from a radiation detector that detects radiation that is generated from the radiation generation unit and is transmitted through a subject.

20. The radiation irradiation device according to claim 19, wherein the body part includes a charging part that charges the radiation detector.

* * * * *